(12) United States Patent
Huber

(10) Patent No.: US 7,109,376 B2
(45) Date of Patent: Sep. 19, 2006

(54) BENZENE AND NAPHTHYLENE DERIVATIVES AND THEIR USE AS UV SCREENING AGENTS

(75) Inventor: Ulrich Huber, Erlenbach (CH)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 11/312,676

(22) Filed: Dec. 19, 2005

(65) Prior Publication Data

US 2006/0153784 A1    Jul. 13, 2006

Related U.S. Application Data

(62) Division of application No. 10/467,430, filed as application No. PCT/EP02/00847 on Jan. 28, 2002, now Pat. No. 7,019,020.

(30) Foreign Application Priority Data

Feb. 5, 2001   (EP) .................. 01102491

(51) Int. Cl.
   *C07C 233/64*   (2006.01)
   *C07C 237/40*   (2006.01)
(52) U.S. Cl. .................................... 564/156
(58) Field of Classification Search ......... None
   See application file for complete search history.

(56) References Cited

FOREIGN PATENT DOCUMENTS

WO   WO 98/16587   * 4/1998

OTHER PUBLICATIONS

Ueno et al., STN International, HCAPLUS Database, Columbus, OH, Accession No. 1998:251223 (2006).*

* cited by examiner

Primary Examiner—Kamal A. Saeed
Assistant Examiner—Andrew B. Freistein
(74) Attorney, Agent, or Firm—Bryan Cave LLP

(57) ABSTRACT

Methods for making UV screening compositions by combining benzoxazolyl benzene derivatives of formula (I):

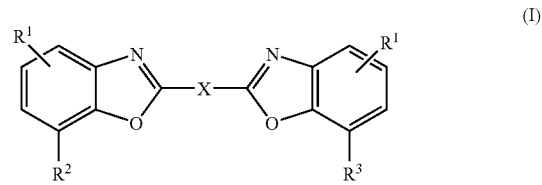

wherein $R^1$ is hydrogen, $C_{1-20}$-alkyl or $C_{2-20}$-alkenyl; $R^2$ and $R^3$ are independently a group $—C(R^4,R^5)C(R^6)=C(R^7,R^8)$ (a) or a group $—C(R^{4'},R^{5'})CH(R^{6'})CH(R^{7'},R^{8'})$ (b), wherein $R^4$, $R^5$, $R^6$, $R^7$, $R^8$, $R^{4'}$, $R^{5'}$, $R^{6'}$, $R^{7'}$ and $R^{8'}$ are independently, hydrogen, $C_{1-10}$-alkyl or $C_{2-10}$-alkenyl, or $C_{2-10}$-alkyl or $C_{3-10}$-alkenyl containing at least one oxygen atom interrupting the hydrocarbon chain; or wherein $R^4$, $R^5$, $R^6$, $R^{4'}$, $R^{5'}$ and $R^{6'}$ are hydrogen, $C_{1-10}$-alkyl or $C_{2-10}$-alkyl containing at least one oxygen atom interrupting the hydrocarbon chain, or alkyl substituted by silane or oligosiloxane moiety, and one of $R^7$ and $R^8$ or $R^{7'}$ and $R^{8'}$ is a silane or oligosiloxane moiety and the other one of $R^7$ and $R^8$ or $R^{7'}$ and $R^{8'}$ is hydrogen; and X is phenylene or naphthylene, or substituted phenylene or naphthylene with a cosmetic base. Methods of protecting a surface from UV radiation by applying a UV screening agent of formula I to a surface such as hair or skin.

1 Claim, No Drawings

BENZENE AND NAPHTHYLENE DERIVATIVES AND THEIR USE AS UV SCREENING AGENTS

This application is a Divisional of prior application Ser. No. 10/467,430 filed Aug. 4, 2003, which is the U.S. National Stage of International Application No.: PCT/EP02/00847 filed Jan. 28, 2002, now U.S. Pat. No. 7,019,020 issued Mar. 28, 2006.

The present invention relates to novel benzoxazolyl benzene derivatives.

More particularly, the invention relates to benzoxazolyl benzene derivatives of the general formula I

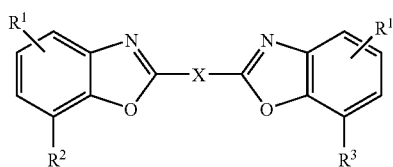

(I)

wherein
$R^1$ is hydrogen, $C_{1-20}$-alkyl or $C_{2-20}$-alkenyl;
$R^2$ and $R^3$ are independently a group —C($R^4$,$R^5$)C($R^6$)=C($R^7$,$R^8$) (a) or a group —C($R^{4'}$,$R^{5'}$)CH($R^{6'}$)CH($R^{7'}$,$R^{8'}$) (b), wherein $R^4$, $R^5$, $R^6$, $R^7$, $R^8$, $R^{4'}$, $R^{5'}$, $R^{6'}$, $R^{7'}$ and $R^{8'}$ are, independently, hydrogen, $C_{1-10}$-alkyl or $C_{2-10}$-alkenyl, or $C_{2-10}$-alkyl or $C_{3-10}$-alkenyl containing at least one oxygen atom interrupting the hydrocarbon chain; or wherein $R^4$, $R^5$, $R^6$, $R^{4'}$, $R^{5'}$ and $R^{6'}$ are hydrogen, $C_{1-10}$-alkyl or $C_{2-10}$-alkyl containing at least one oxygen atom interrupting the hydrocarbon chain, or alkyl substituted by a silane or oligosiloxane moiety, and one of $R^7$ and $R^8$ or $R^{7'}$ and $R^{8'}$ is a silane or oligosiloxane moiety and the other one of $R^7$ and $R^8$ or $R^{7'}$ and $R^{8'}$ is hydrogen; and
X is phenylene or naphthylene, or substituted phenylene or naphthylene.

In another aspect, the present invention relates to novel UV screening compositions, particularly topical compositions for cosmetic or dermatological use; and to the use of compounds of formula I as defined above as UV screening agents, particularly for protecting human skin or hair against UV radiation.

As used herein, $C_1$–$C_{20}$-alkyl and $C_1$–$C_{10}$-alkyl denote straight chain or branched saturated hydrocarbon residues with 1 to 20 (or 1 to 10) carbon atoms, such as methyl, ethyl, propyl, isopropyl, thexyl, (1,1,2 dimethylpropyl), n-butyl, sec. butyl, tert. butyl, pentyl, neopentyl, hexyl, 2-ethyl-hexyl, octyl and the like.

$C_2$–$C_{20}$-alkenyl and $C_2$–$C_{10}$-alkenyl denote straight chain or branched hydrocarbon residues with 2 to 20 (or 2–10) carbon atoms and containing at least one C—C double bond, such as vinyl, allyl, 2-butenyl, methallyl, 2-penten-3-yl, 3-hexen-2-yl, 3-hepten-2-yl, 3-octen-2-yl, 1-octen-3-yl and 2-octen-1-yl.

The term "$C_2$–$C_{10}$-alkyl containing at least one oxygen atom interrupting the hydrocarbon chain" denotes straight chain or branched saturated hydrocarbon residues with 2 to 10 carbon atoms which are bound via a carbon atom and have at least one —CH$_2$O— group, such as methoxymethyl, 4-oxa-hexyl, 4,7-dioxa-nonyl and 4,7,10-trioxa-dodecyl. Similarly, the term "$C_3$–$C_{10}$-alkenyl containing at least one oxygen atom interrupting the hydrocarbon chain" denotes straight chain or branched olefinically unsaturated hydrocarbon residues with 3 to 10 carbon atoms which are bound via a carbon atom and have at least one —CH$_2$O— group and at least one C—C double bond.

A silane moiety is, e.g., a group —Si$R^a R^b R^c$, wherein $R^a$, $R^b$ and $R^c$ each independently are $C_1$–$C_6$alkyl or phenyl. Preferred silane moieties are trimethylsilane, triethylsilane, tripropylsilane, triisopropylsilane, dimethyl tert.butylsilane, dimethyl thexylsilane, triphenylsilane, dimethylphenylsilane and the like.

An oligosiloxane moiety is, e.g., a group of the general formula IVa, IVb or IVc

(IVa)

(IVb)

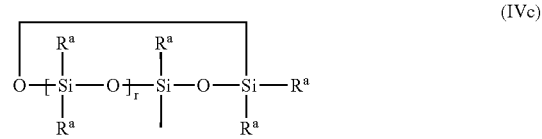
(IVc)

wherein m=0, 1 or 2; n=1, 2 or 3 and m+n=3, $R^a$ and $R^b$ are $C_1$–$C_6$ alkyl or phenyl, preferably $C_1$–$C_4$ alkyl, more preferably methyl, and r is an integer from 1 to 9, preferably 1 to 3. Preferred oligosiloxane moieties are —SiMe$_2$(OSiMe$_3$) and —SiMe (OSiMe$_3$)$_2$ wherein Me is methyl.

If X is substituted phenylene or naphthylene, the substituents may be 1 or 2 hydroxly or $C_{1-20}$alkoxy groups. Preferably, X is unsubstituted p-phenylene or 1,4-naphthylene, and, most preferably, p-phenylene.

The compounds of formula I preferably contain a lipophilic or a sterically hindered substituent $R^1$, $R^2$ or $R^3$. Examples of lipophilic substituents are silane or oligosiloxane moieties, and alkyl or alkenyl groups having 5 or more, preferably 8 or more carbon atoms, such as 2-ethyl-hexyl, decyl, dodecyl, 3-octen-2-yl, 1-octen-3-yl, and 2-octenyl. A sterically hindered substituent suitably is an alkyl group having a tertiary carbon atom, such as isopropyl, or quaternary carbon atom, such as tert.-butyl, tert.-amyl (2-methyl-2-pentyl), and 2,4-trimethyl-2-pentyl.

Preferred compounds of the formula I above are those wherein $R^2$ and $R^3$ are a group (a) as defined above wherein $R^5$, $R^6$ and $R^7$ are hydrogen and $R^4$ and $R^8$ are $C_1$–$C_{10}$-alkyl, particularly those wherein $R^4$ is methyl and $R^8$ is $C_3$–$C_5$-alkyl; or wherein $R^5$, $R^6$, $R^7$ and $R^8$ are hydrogen and $R^4$ is $C_1$–$C_{10}$-alkyl, particularly $C_3$–$C_5$-alkyl. Further, compounds of formula I wherein $R^2$ and $R^3$ are a group (b) as defined above wherein $R^{5'}$, $R^{6'}$, $R^{7'}$ are hydrogen and $R^{4'}$ and $R^{8'}$ are $C_1$–$C_{10}$-alkyl, particularly when $R^{4'}$ is methyl and $R^{8'}$ is $C_3$–$C_5$-alkyl are preferred. Finally, compounds of formula I wherein $R^2$ and $R^3$ are a group (b) as defined above wherein $R^{5'}$, $R^{6'}$, $R^{7'}$ are hydrogen and $R^{8'}$ is an oligosiloxane moiety, or wherein $R^{4'}$, $R^{5'}$ and $R^{7'}$ are hydrogen, $R^{6'}$ is $C_1$–$C_{10}$-alkyl and $R^{8'}$ is an oligosiloxane moiety and compositions containing such compounds are preferred.

The compounds of the general formula I can be prepared by alkylating a compound of the general formula II

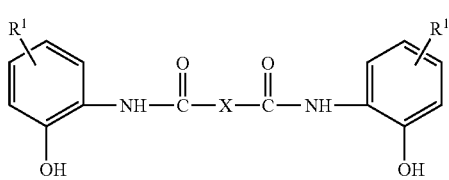

wherein X and $R^2$ are as defined above, with a compound of the general formula $Y-R^{21}$, wherein Y is a leaving group and $R^{21}$ is $-C(R^4,R^5)C(R^6)=C(R^7,R^8)$, wherein $R^4$, $R^5$, $R^6$, $R^7$ and $R^8$ are, independently, hydrogen, $C_{1-10}$-alkyl or $C_{2-10}$-alkenyl, or $C_{2-10}$-alkyl or $C_{3-10}$-alkenyl containing at least one oxygen atom interrupting the hydrocarbon chain; to yield a compound of the general formula III

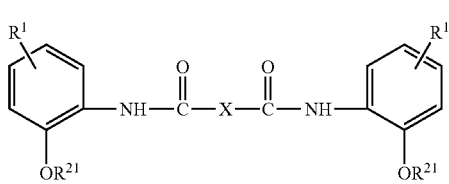

wherein X, $R^1$ and $R^{21}$ are as defined above, heating the compound of the general formula III to yield a compound of the general formula I wherein X and $R^1$ are as defined above and $R^2$ and $R^3$ are a group $R^{21}$ as defined above, and, if desired, either reacting the so-obtained compound of the general formula I with a silane or oligosiloxane carrying a free SiH group to obtain a compound of the general formula I wherein $R^2$ and $R^3$ are a group $-C(R^4,R^5)CH(R^6)C(R^7,R^8)$, wherein one of $R^7$ and $R^8$ is hydrogen and the other one of $R^7$ and $R^8$ is a silane or oligosiloxane moiety, and $R^4$, $R^5$ and $R^6$ are hydrogen, $C_1-C_{10}$-alkyl or $C_2-C_{10}$-alkyl containing at least one oxygen atom interrupting the hydrocarbon chain, or $C_1-C_{10}$-alkyl substituted by a silane or oligosiloxane moiety; or hydrogenating the so-obtained compound of formula I to obtain a compound of the general formula I wherein $R^2$ and $R^3$ are $-C(R^4,R^5)CH(R^6)C(R^7,R^8)$, wherein $R^4$, $R^5$, $R^6$, $R^7$ and $R^8$ are hydrogen or $C_1-C_{10}$-alkyl or $C_2-C_{10}$-alkyl containing at least one oxygen atom interrupting the hydrocarbon chain.

In the first reaction step the compound of formula II is reacted with a compound of formula $Y-R^{21}$. The leaving group Y may be any conventional leaving group such as halogen, e.g., chloro, bromo, or a sulfonyloxy group, e.g., tosyloxy or mesyloxy. The reaction can be carried out in a manner known per se for the alkylation of phenolic hydroxy groups, i.e., in the presence of a base such as an alkali carbonate, e.g., sodium carbonate, alkali hydroxide or alkali alcoholates, e.g., sodium methylate; an amine such as triethyl amine, N,N-dimethylamino pyridine or 1,4-diazabicyclo[2.2.2]octane (DABCO); in a polar solvent e.g., an alcohol such as n-butanol, an ether such as diethyleneglycol mono-methyl ether, tetrahydrofuran or dioxan; or in dimethyl formamide, dimethyl sulfoxide, N,N-dimethyl propylene urea or 1-methylpyrrolidone, or in a solvent which simultaneously may serve as a base, such as N,N-dimethylamino pyridine, at temperatures from room temperature up to the boiling point of the reaction mixture. The phenol ether of the formula III obtained can be rearranged by heating, suitably to a temperature of from 50 to 300° C., if desired, in a solvent, suitably in a solvent that is conventionally used in Claisen rearrangements, e.g., in diethyl aniline or trichloro benzene. In the same reaction step, ring closure to form the oxazole ring takes place, thus yielding a compound of formula I wherein X and $R^1$ are as defined above, and $R^2$ and $R^3$ are a group (a) as defined above.

The Claisen rearrangement may result in the formation of isomers with respect to the structure and bonding site of the groups $R^2$ and $R^3$. While these isomers may be separated by conventional methods such as chromatography it is preferred to use such mixture of isomers in the compositions of the present invention if they are obtained in the Claisen rearrangement.

If desired, a compound of the formula I wherein $R^2$ and $R^3$ are a group (a) can be hydrosilylated by reaction with a silane, oligosiloxane or polysiloxane carrying a free SiH group. The hydrosilation reaction is suitably carried out in the presence of a transition metal catalyst e.g. a platinum catalyst such as platinum on charcoal, or a platinum complex catalyst such as e.g. divinyl-tetramethyl disiloxane platinum, ammonium hexachloroplatinate (IV), hydrogen hexachloroplatinate (IV) hydrate, or a Rhodium catalyst, e.g. $Rh_2Cl_2$ (cyclooctadiene)$_2$ in a suitable reaction solvent such as e.g. in toluene. The reactants are usually present in about equal molar amounts and the reaction is carried out at a somewhat elevated temperature, e.g. at about 60° C.–150° C., preferably at about 40° C.–100° C., more preferably at about 80° C.

Alternatively, an alkenyl group in a compound of the formula I wherein $R^2$ and $R^3$ are a group (a) can be hydrogenated. The hydrogenation can be carried out by methods known per se for the hydrogenation of olefinic double bonds, e.g. with elemental hydrogen in the presence of a noble metal catalyst such as Pd, or with Raney-Ni, preferably with elemental hydrogen in the presence of an appropriate catalyst which does not attack the triazole ring, e.g., a partially inactivated noble metal catalyst such as a Lindlar catalyst.

By the process of the present invention, the compounds of the general formula I may be obtained as mixtures of isomers of the substituents $R^2$ and $R^3$ depending on the conditions of the Claisen rearrangement of the compounds of the formula III.

The starting compounds of formula II inasmuch as they are not known or described hereinafter can be prepared in analogy to methods known per se or described hereinafter. Thus, terephthalic acid (or naphthaline-1,4-dicarboxylic acid) or a reactive derivative thereof such as an acid halogenide can be reacted with o-amino phenol which may be substituted by a substituent as defined for $R^1$.

The compounds of the general formula I are photostable and have strong absorption maxima in the UV-A region with ε values up to 58,000 and a steep downgrade of the absorption curve towards higher wave lenghts. Accordingly, they can be used as UV screening agents, especially in preparations for skin protection and sunscreen preparations for everyday cosmetics, which may comprise a compound of formula I in a cosmetic base which is conventional for such preparations and which may contain other conventional UV-A and/or UV-B filters. Said combinations of UV filters can show a synergistic effect. The manufacture of said light screening preparations is well known to the skilled artisan in this field. The amount of compounds of the general formula I and other known UV-filters is not critical. Suitable amounts are about 0.5 to about 12% of a sunscreen agent, i.e., a compound of formula I either alone or in combination with other UV filters. The compounds of the general formula I exhibit good lipophilicity and thus can be incorporated well into oil and fat containing topical preparations. In the preparations a mixture of compounds of formula I may be present.

Suitable UV B filters, i.e. substances having absorption maxima between about 290 and 320 nm, for combination with the compounds of the formula I are for example the following:

Acrylates such as 2-ethylhexyl 2-cyano-3,3-diphenylacrylate (octocrylene, PARSOL 340), ethyl 2-cyano-3,3-diphenylacrylate and the like;

Camphor derivatives such as 4-methyl benzylidene camphor (PARSOL 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

Cinnamate derivatives such as octyl methoxycinnamate (PARSOL MCX), ethoxyethyl methoxycinnamate, diethanolamine methoxycinnamate (PARSOL Hydro), isoamyl methoxycinnamate and the like as well as cinnamic acid derivatives bond to siloxanes;

Organosiloxane compounds containing benzmalonate groups as described in EP 358584 B1, EP 538,431 B1 and EP 709,080 A1;

Pigments such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Imidazole derivatives such as e.g. 2-phenyl benzimidazole sulfonic acid and its salts (PARSOL HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomenthyl salicylate (homosalate, HELIOPAN) and the like;

Triazone derivatives such as octyl triazone (UVINUL T-150), dioctyl butamido triazone (UVASORB HEB) and the like.

Suitable UV A filters i.e. substances having absorption maxima between about 320 and 400 nm, for combination with the compounds of the formula I are for example the following:

Dibenzoylmethane derivatives such as 4-tert.butyl-4'-methoxydibenzoyl-methane (PARSOL 1789), dimethoxy-dibenzoylmethane, isopropyldibenzoylmethane and the like;

Benzotriazole derivatives such as 2,2'-methylene-bis-(6-(2H-benzotriazole-2-yl)-4-(1,1,3,3,-tetramethylbutyl)-phenol (TINOSORB M) and the like;

Pigments such as microparticulated ZnO and the like. The term "microparticulated" refers to a particle size from about 5 nm to about 200 nm, particularly from about 15 nm to about 100 nm. The ZnO particles may also be coated by metal oxides such as e.g. aluminum or zirconium oxides or by organic coatings such as e.g. polyols, methicone, aluminum stearate, alkyl silane. Such coatings are well known in the art.

As dibenzoylmethane derivatives are photolabile it is necessary to photostabilize these UV-A screening agents. Thus, dibenzoylmethane derivatives such as e.g. PARSOL 1789 when used in combination with the compounds of formula I can be stabilized by the following stabilizing agents:

3,3-diphenylacrylate derivatives as described in EP 514,491 B1 and EP 780,119 A1;

benzylidene camphor derivatives as described in U.S. Pat. No. 5,605,680;

organosiloxanes containing benzmalonate groups as described in EP 358,584 B1, EP 538,431 B1 and EP 709,080 A1.

Further, UV screening agents absorbing in the region overlapping UV-A and UV-B such as those disclosed in EP 895,776 and EP 780,382 may be used as additional ingredients in the compositions of the present invention.

As cosmetic bases conventional for light screening compositions in the scope of the present invention there can be used any conventional preparation which corresponds to the cosmetic requirements, e.g. creams, lotions, emulsions, salves, gels, solutions, sprays, sticks and milks; see also Lowe and Shaath (eds.), Sunscreens, Development, Evaluation and Regulatory Aspects, Marcel Dekker, Inc. New York and Basel (1990).

The invention is illustrated further by the Examples which follow.

EXAMPLE 1

Preparation of 1,4-bis-[2-(5-tert.-butyl-7-allyl-benzoxazol)-yl]-benzene (a) Terephtalic acid chloride: To 40.9 g of terephtalic acid in 250 ml of toluene and 3.3 ml of pyridine, 41.1 ml of thionylchloride was slowly added at a temperature between 22 and 35° C. The reaction mixture was heated to 80° C. for four hours. From the cooled reaction mixture a blue precipitate was filtered off and the yellow solution was concentrated under reduced pressure and dried at high vacuum to yield a crude liquid which was used in (b).

(b) N,N'-bis-(2-hydroxy-5-tert.-butyl-phenyl)-terephtalamide: To 12.4 g of 2-amino-4 tert.-butylphenol (Aldrich Co.) in 50 ml of 1-methyl-pyrrolidone under nitrogen atmosphere there was added 7.26 g of terephtalic acid chloride as obtained in (a), followed by 6.1 ml of pyridine. The mixture was heated to 80° C. for 19 hours and the reaction traced by TLC (methylene chloride: methanol=12:1). Then the reaction mixture was cooled to 20° C., poured on a mixture of methanol/water=1:1, and filtered. The residue was washed three times with water and dried at 80° C. for three days and at high vacuum at 150° C. for five hours. 16.1 g (97%) of crude crystals were obtained (m.p. >250° C.).

(c) N,N'-Bis-(2-allyloxy-5-tert.-butyl-phenyl)-terephtalamide: To 10 g of the above N,N'-bis-terephtalamide in 138 ml of 1-methyl-pyrrolidone, 11.4 g of anhydrous sodium carbonate and a trace of potassium iodide, 4.2 ml of allyl-bromide was slowly added by means of a syringe under nitrogen atmosphere. A solid material was formed in the dark, reddish solution. The mixture was heated to 70° C. for 18 hours and the reaction was traced by TLC (ethyl acetate: bexane=1:1). Then the reaction mixture was cooled to 10° C.

A precipitate was formed, which was filtered off, washed with water and dried at 80° C. for four days in a vacuum. 10.5 g (84%) of crude crystals were obtained (m.p. 172–173° C.), which were identified by UV: 311 nm (E=332, in $CH_2Cl_2$), NMR and MS: 540($M^+$), 499, 441, 336 (100%).

(d) 1,4-Bis-[2-(5-tert.-butyl-7-allyl-benzoxazol)-yl]-benzene: 10 g of the allyl ether as obtained in step (c) was heated in a Kugelrohr apparatus for 15 hours at 200° C.: The reaction was followed by TLC (ethyl acetate: hexane=1:1). There were obtained 9.3 g (100%) of brown crystals (m.p. 163–165° C.), which were identified by NMR and MS: 504($M^+$), 489 (100%), 433, 237.

This product was 1.1% soluble in Cétiol LC (Cocoyl cyprylate caprate). It was irradiated in high dilution with a Hg-lamp 150 W (Heraeus) and shown to be photostable.

EXAMPLE 2

Preparation of 1,4-bis-[2-(5-tert.-butyl-7-{3-(1,1,3,3, 3-pentamethyl-disiloxanyl)-1-propyl}-benzoxazol)-yl]-benzene To 1.6 g of the bis-(allyl-benzoxazole)-benzene obtained in Example 1 in 45 ml of toluene 1.5 g of pentamethyldisiloxane (Fluka) were added and a trace of divinyl tetramethyl disiloxane platinum complex under strict nitrogen atmosphere. The reaction mixture was heated to 80° C. for 18 hours and then evaporated to obtain 3 g of a brown oil. After chromatography in hexane/ether slightly yellow crystals were formed. M.p. 89–90° C. UV($CH_2Cl_2$) 350 nm (E=551); MS: 800 ($M^+$), 772, 610, 147 (100%).

The solubility of this product was determined for Cétiol LC (Cocoyl cyprylate caprate)=18%. The product was irradiated in high dilution with a Hg-lamp 150 W (Heraeus) and shown to be photostable.

EXAMPLE 3

Preparation of 1,4-bis-[2-(7-{3-(1,1,3,3,3-pentamethyl-disiloxanyl)-1-isobutyl}-benzoxazol)-yl]-benzene (a) N,N'-Bis-(2-hydroxy-phenyl)-terephtalamide: To 7.9 g of 2-amino-phenol (Fluka) in 60 ml of 1-methyl-pyrrolidone under nitrogen atmosphere 7.26 g of terephtalic acid chloride [see example 1(a)] were added, followed by 6 ml of pyridine. The mixture was heated to 80° C. overnight. The reaction was traced by TLC. (methylene chloride: methanol=12:1). Then the reaction mixture was cooled to 20° C., poured on a mixture of methanol/-water=1:1, and filtered. The crystalline, yellow residue was washed three times with water and dried at 80° C. at high vacuum. There were obtained 10.7 g (89%) of crude crystals (m.p. >250° C.), which were identified by NMR and used in step (b).

(b) N,N'-bis-(2-methallyloxy-phenyl)-terephtalamide: To 4 g of N,N'-bis-terephtalamide as obtained in (a) in 40 ml of 1-methyl-pyrrolidone, 6.3 g of anhydrous sodium carbonate and a trace of potassium iodide, 2.8 ml of methallylchloride was slowly added by means of a syringe under nitrogen atmosphere. The mixture was heated to 80° C. overnight and the reaction was traced by TLC. (ethyl acetate: hexane=1:1). Then the reaction mixture was cooled to 10° C. and water was added. A precipitate was formed, which was filtered off, washed with water and dried. 4.8 g (80%) of a pale yellow solid was obtained, which was identified by HPLC and NMR ($CDCl_3$): 1.87 ppm (S/6Pr); 4.56 (S/4Pr); 5.06 (S/2Pr); 5.12 (S/2Pr); 6.94 (D×D/2Pr); 7.04 (M/4Pr); 8.00 (S/4Pr); 8.54 (D×D/2Pr); 8.69 (S/2Pr, NH).

(c) 1,4-Bis-[2-(7-methallyl-benzimidazol)-yl]-benzene: 4 g of the allyl ether obtained in (b) in 50 ml of 1,2,4-trichlorobenzene was heated to reflux in a 100 ml reaction flask for 10 hours. The reaction was followed by TLC. (ethyl acetate: hexane=1:3). The reaction mixture was concentrated and chromatographed on silicagel to yield 0.5 g of yellowish crystals which were identified by HPLC and NMR ($CDCl_3$): 1.80 ppm (S/6Pr); 3.70 (S/4Pr); 4.87 (S/2Pr); 4.91 (S/2Pr); 7.20 (D/2Pr); 7.32 (Tr/2Pr); 7.67 (D/4Pr): 8.40 (S/2Pr); 8.69 (S/2Pr, NH).

(d) 1,4'-Bis-[2-(7-{3-(1,1,3,3,3-pentamethyl-disiloxanyl)-1-isobutyl}-benzoxazol)-yl]-benzene: To 0.45 g of the bis-(methallyl-benzoxazole)-benzene obtained in (c) in 10 ml of toluene 0.5 ml of pentamethyldisiloxane (Fluka) were added and 0.05 ml of 20% solution of divinyl tetramethyl disiloxane platinum complex in toluene under strict nitrogen atmosphere. The reaction mixture was heated to 80° C. overnight and then evaporated. After chromatography in hexane/ether, 0.59 g (75%) of a brownish oil was obtained, which slowly crystallized. M.p. ca. 38° C. UV($CH_2Cl_2$) 344 nm (E=736); MS: 716 ($M^+$), 701, 674, 147 (100%).

The solubility of this product was determined for Crodamol DA (diisopropyladipate)=5.03%. The product was irradiated in high dilution with a Hg-lamp 150 W (Heraeus) and shown to be photostable.

EXAMPLE 4

Preparation of 1,4-bis-[2-(5-tert.-butyl-7-methallyl-benzoxazol)-yl]-benzene (a) N,N'-bis-(2-methallyloxy-5-tert.-butyl-phenyl)-terephtalamide: To 2.76 g of N,N'-bis-(2-hydroxy-5-tert.-butyl-phenyl)-terephtalamide [see Example 1(b)], dissolved in 38 ml of 1-methyl-pyrrolidone, 3.15 g of anhydr. sodium carbonate and a trace of potassium iodide. 1.35 ml of methallylchloride was slowly added by means of a syringe under nitrogen atmosphere. The mixture was heated to 70° C. for 18 hours and the reaction was traced by TLC. (methylene chloride: methanol=4:1). Then the reaction mixture was cooled to 10° C. and poured on 200 ml of water. This mixture was extracted twice with 100 ml of ethyl acetate. The organic phases were washed with water, 2n NaOH and brine, dried with $Na_2SO_4$ and concentrated. The residue was recrystallised from toluene to yield 1.45 g (42%) of beige crystals (m.p. 184–185° C.), which were identified by UV: 311 nm (E=291, in $CH_2Cl_2$), NMR and MS: 568 ($M^+$), 513, 350 (100%).

(b) 1,4-Bis-[2-(5-tert.-butyl-7-methallyl-benzoxazol)-yl]-benzene: 1.29 g of the allyl ether obtained in (a) and a trace of boric acid in 10 ml of 1,2,4-trichlorobenzene was heated to reflux in a 100 ml reaction flask for 4.5 hours. The reaction was followed by TLC. (ethyl acetate: hexane=1:3). The reaction mixture was concentrated and precipitated with hexane and chromatographed on silicagel to yield 0.62 g (51%) of yellowish crystals (m.p. 146–149° C.) which were identified by UV($CH_2Cl_2$): 349 nm (E=1015), NMR and MS: 532($M^+$, 100%), 517, 251.

EXAMPLE 5

Preparation of 1,4-bis-[2-(5-tert.-butyl-7-{3-(1,3,3, 3-tetramethyl-1-[(tri-methyl-silyl)-oxy]-disiloxanyl)-1-isobutyl}-benzoxazol)-yl]-benzene A 25 ml round bottom flask equipped with a magnetic stirrer, a reflux condenser and an oil bath under nitrogen atmosphere was charged with 0.4 g of bis-(methallyl-benzoxazole)-benzene [Example 4(b)] in 10 ml of tetrahydrofuran. 0.43 ml of 1,1,1,3,5,5,5-heptamethyl-trisiloxane (Rhodia) and 0.05 ml of 20% solution of divinyl tetramethyl disiloxane platinum complex in toluene was added under strict nitrogen atmosphere. The reaction mixture was refluxed during 70 hours and then evaporated. After chromatography in hexane/ethylacetate, 0.81 g (42%) of brownish crystals were obtained (m.p. 72–73° C.). UV(CH$_2$Cl$_2$) 350 nm (E=615); MS: 934 (M$^+$), 714, 698, 221 (100%).

The solubility of this product was determined for Cétiol LC (Cocoyl cyprylate caprate)=12.3%. The product was irradiated in high dilution with a Hg-lamp 150 W (Heraeus) and shown to be photostable.

EXAMPLE 6

Preparation of 1,4-bis-[2-(5-methyl-7-oct-3-en-2-yl-benzoxazol)-yl]-benzene (a) N,N'-Bis-(2-hydroxy-5-methyl-phenyl)-terephtalamide: In analogy to Example 1(b) but substituting 2-amino-4-methylphenol (Fluka) for 2-amino-4-tert.-butylphenol there was obtained N,N'-bis-(2-hydroxy-5-methyl-phenyl)-terephtalamide, yellow crystals which were identified by NMR (DMSO): 2.24 ppm (S/6Pr); 6.80–6.89 (M/4Pr); 7.5 (D/2Pr); 8.10 (S/4Pr); 9.50 (S, broad/2Pr); 9.65 (S/2Pr). Yield 96%.

(b) N,N'-bis-(2-oct-2-enyloxy-5-methyl-phenyl)-terephtalamide: To 5 g of the above N,N'-bis-terephtalamide in 40 ml of 1-methyl-pyrrolidone, 7 g of anhydrous sodium carbonate and 2 mg of potassium iodide 6.4 g (33.3 mmol) of 1-bromo-2-octene (prepared from 1-octene-3-ol by the method of Miginiac and Mauzé, Bull. Soc. Chim. France 2544, 2547 (1968) were slowly added by means of a syringe. The reaction mixture was left to stir for two hours at room temperature and for 18 hours at 80° C. The reaction was traced by TLC. (hexane: ethylacetate=1:1). Then the reaction mixture was cooled to 20° C., poured into water and the precipitate was filtered and washed with water and dissolved in ether. Residual solid salts were removed and the organic phase was concentrated and dried at high vacuum to yield 6.44 g (81%) of a brown solid, which was identified by NMR (CDCl$_3$): 0.87 ppm (Tr/6Pr); 1.20–1.44 (M/12Pr); 2.09 (D×Tr/4Pr); 2.35 (S/6Pr); 4.57 (D/4Pr); 5.69–5.74 (M/2Pr); 5.82–5.88 (M/2Pr); 6.82–6.89 (M/4Pr); 8.00 (S/4Pr); 8.38 (S/2Pr); 8.65 (S/2Pr).

(c) 1,4-Bis-[2-(5-methyl-7-oct-3-en-2-yl-benzoxazol)-yl]-benzene: 4.5 g (7.6 mmol) of the above N,N'-bis-(2-oct-2-enyloxy-5-methyl-phenyl)-terephtalamide in 40 ml of N,N-diethylaniline was heated to reflux (230° C.). The reaction was traced by TLC. (hexane: ethyl acetate=3:1). After 66 hours the reaction was completed, and a solution of 2n HCl was added to the cold reaction mixture, followed by extraction with ether (3×). The combined organic phases were washed with a 10% KOH solution, and the latter was acidified to pH 3–4 with 5n HCl and extracted with ether. The combined ether phases were dried over sodium sulfate and concentrated to yield 2.74 g (64%) of a white solid, which contained about 90% of the product defined above and 10% of 1,4-bis-[2-(5-methyl-7-pentyl-allyl-benzoxazol)-yl]-benzene. The latter group was formed by a normal Claisen rearrangement in contrast of the 7-(oct-3-en-2-yl) group, which was formed by an abnormal Claisen rearrangement according to Schmid et al., Helv. Chim. Acta 51:1603 (1968). M.p. 118–20° C. UV(CH$_2$Cl$_2$): 349 nm (E=690); MS: 560 (M+), 477, 159 (100%), 145.

The solubility of this product mixture was determined for Crodamol DA (diisopropyladipate)=1.33%. The product was irradiated in high dilution with a Hg-lamp 150 W (Heraeus) and shown to be photostable.

EXAMPLE 7

Preparation of 1,4-bis-[2-(5-tert.-butyl-7-(1-pentyl-allyl)- and/or -7-(oct-3-en-2-yl)benzoxazol)-yl]-benzene (a) N,N'-Bis-(2-oct-2-enyloxy-5-tert.-butyl-phenyl)-terephtalamide: In analogy to Example 6(b), but substituting N,N'-bis-(2-hydroxy-5-tert.-butyl-phenyl)-terephtalamide (Example 1b) for N,N'-bis-(2-hydroxy-5-methyl-phenyl)-terephtalamide there was obtained, after chromatography, 53% of N,N'-bis-(2-oct-2-enyloxy-5-tert.-butyl-phenyl)-terephtalamide, which was identified by MS and NMR (CDCl$_3$): 0.874 ppm (Tr/6Pr); 1.2–1.36 (M/30Pr); 2.08 (M/4Pr); 4.58 (D/4Pr); 5.7 (Tr×D/2Pr); 5.88 (Tr×D/2Pr); 6.87 (D/2Pr); 7.08 (D/2Pr); 8.01 (S/4Pr) and 8.65 (S, broad/4Pr).

(b) 1,4-bis-[2-(5-tert.-butyl-7-(1-pentyl-allyl)- and/or -7-(oct-3-en-2-yl)benzoxazol)-yl]-benzene: 1.6 g (2.3 mmol) of the above N,N'-bis-(2-oct-2-enyloxy-5-tert.-butyl-phenyl)-terephtalamide in 15 ml of 1,2,4-trichlorobenzene was heated to reflux (210° C.) under nitrogen atmosphere over night. The reaction was traced by TLC. (hexane: ethyl acetate=3:1). The solvent was evaporated at the Kugelrohr apparatus. 1.4 g (92%) of a dark liquid was obtained, which after chromatography yielded 0.8 g (52%) of the bis-[2-benzoxazol-yl]-benzene product, comprising an isomer carrying the 7-(pentyl-allyl) group in a proportion of about 58% and an isomer carrying the 7-(oct-2-en-1-yl) group in a proportion of about 42%, tentatively referred to herein as 1,4-bis-[2-(5-tert.-butyl-7-(1-pentyl-allyl)(and/or -7-oct-3-en-2-yl)-benzoxazol)-yl]-benzene. UV(CH$_2$Cl$_2$) 349 nm (E=715); MS: 544 (M$^+$100%), 629, 534, 517.

The product was easily mixable with conventional cosmetic solvents. This product was irradiated in high dilution with a Hg-lamp 150 W (Heraeus) and was shown to be photostable.

EXAMPLE 8

Preparation of 1,4-bis-[2-(5-tert.-butyl-7-oct-3-en-2-yl-benzoxazol)-yl]-benzene In analogy to Example 6(c), but substituting N,N'-bis-(2-oct-2-enyloxy-5-tert.-butyl-phenyl)-terephtalamide [Example 7(a)] for N,N'-bis-(2-oct-2-enyloxy-5-methyl-phenyl)-terephtalamide there was obtained, after heating for three nights to 230° C. and chromatography, a liquid product in 85% yield, which was identified to be mainly the product defined above, formed by an abnormal Claisen rearrangement. UV(CH$_2$Cl$_2$) 350 nm (E=804); MS: 644 (M$^+$), 629, 587, 561, 55 (100%).

The product was easily mixable with conventional cosmetic solvents. This product was irradiated in high dilution with a Hg-lamp 150 W (Heraeus) and was shown to be photostable.

EXAMPLE 9

Preparation of 1,4-bis-[2-(7-oct-3-en-2-yl-benzoxazol)-yl]-benzene (a) N,N'-Bis-(2-oct-2-enyloxy-phenyl)-terephtalamide: In analogy to Example 6(b) but substituting N,N'-bis-(2-hydroxy-phenyl)-terephtalamide [Example 2(b)] for N,N'-bis-(2-hydroxy-5-methyl-phenyl)-terephtalamide there were obtained, after chromatography, 69.5% of yellow crystals which were identified by NMR (CDCl$_3$): 0.87 ppm (Tr/6Pr); 1.27–1.43 (M/12Pr); 2.1 (Tr×D/4Pr); 4.6 (D/4Pr); 5.72 (Tr× D/2Pr); 5.87 (Tr×D/2Pr); 6.94 (D/2Pr); 7.0–7.1 (M/4Pr); 8.01 (S/4Pr); 8.54 (D/2Pr) and 8.67 (S, broad/2Pr).

(b) 1,4-Bis-[2-(7-oct-3-en-2-yl-benzoxazol)-yl]-benzene: In analogy to Example 6(c) but substituting N,N'-bis-(2-oct-2-enyloxy-phenyl)-terephtalamide [Example 9(a)] for N,N'-bis-(2-oct-2-enyloxy-5-methyl-phenyl)-terephtalamide there was obtained, after recrystallisation from ethanol, a pale yellowish powder (m.p. 87–89° C.) in 51% yield, which was identified to be mainly the product defined above, formed by an abnormal Claisen rearrangement). UV(CH$_2$Cl$_2$) 344 nm (E=1085); MS: 532 (M$^+$), 629, 517, 475, 449, 145 (100%).

The solubility of this product was determined for Cétiol LC (Cocoyl cyprylate caprate)=1.02%. The product was irradiated in high dilution with a Hg-lamp 150 W (Heraeus) and was shown to be photostable.

EXAMPLE 10

Preparation of 1,4-bis-[2-(4-(or 5-)tert.-pentyl-7-(1-pentyl-allyl)(and/or -7-oct-3-en-2-yl)-benzoxazol)-yl]-benzene (a) 4- and 5-tert.-pentyl-2-aminophenol: A mixture of 1 g of 2-amino-phenol (Fluka) dissolved in 20 ml of methanesulfonic acid and 1.4 ml of 2-chloro-2-methylbutane was heated to 70° C. for four hours. The reaction mixture was poured on diluted NaOH with ice and extracted three times with ether. The dried and concentrated organic phases were chromatographed to yield 0.8 g (49%) of a mixture of 4-(27%) and 5-(73%) tert.-pentyl-2-aminophenol. MS: 179 (M$^+$), 150 (100%).

(b) N,N'-bis-(2-hydroxy-4-(27% share) and 5-(73% share) tert.-pentyl-phenyl)-terephtalamide: In analogy to Example 1(b) but substituting the above 4-(and 5-)tert.-pentyl-2-aminophenol for 2-amino-4-tert.-butylphenol there were obtained yellow crystals in 92% yield, which were identified by NMR (DMSO): 0.66 ppm (Tr/6Pr); 1.22 and 1.27 (2×S/12Pr); 1.59 (Q/4Pr); 6.87 (D/2Pr); 7.03 and 7.10 (2×D/2Pr); 7.61 and 7.66 (2×S/2Pr); 8.11 (S/4Pr); 9.44 (S/2Pr); 9.75 (S/2Pr).

(c) N,N'-Bis-(2-oct-2-enyloxy-4-(and 5-)tert.-pentyl-phenyl)-terephtalamide: In analogy to Example 6(b), but substituting the above N,N'-bis-(2-hydroxy-4-(27% share) and 5-(73% share)tert.-pentyl-phenyl)-terephtalamide for N,N'-bis-(2-hydroxy-5-methyl-phenyl)-terephtalamide there was obtained the above product which was identified by MS: 709 (M$^+$), 598, 488, 310 (100%).

d) 1,4-Bis-[2-(4-resp.5-tert.-pentyl-7-oct-3-en-2-yl-benzoxazol)-yl]-benzene: In analogy to Example 6(c) but substituting the above N,N'-bis-(2-oct-2-enyloxy-4-(and 5)tert.-pentyl-phenyl)-terephtalamide for N,N'-bis-(2-oct-2-enyloxy-5-methyl-phenyl)-terephtalamide there was obtained after chromatography a liquid mixture of isomeric products, tentatively referred to herein as 1,4-bis-[2-(4-(or 5-)tert.-pentyl-7-(1-pentyl-allyl)(and/or -7-oct-3-en-2-yl)-benzoxazol)-yl]-benzene which were identified by NMR, UV(EtOH): 350 nm (E=736), 368 nm (E=474) and MS: 673 (M$^+$), 643 (100%), 307.

The product was easily mixable with conventional cosmetic solvents. This product was irradiated in high dilution with a Hg-lamp 150 W (Heraeus) and was shown to be photostable.

EXAMPLE 11

Preparation of 1,4-bis-[2-(5-tert.-butyl-7-oct-2-yl-benzoxazol)-yl]-benzene

A 50 ml three necked reaction flask equipped with an effective stirrer and low pressure hydrogen access was charged with 0.5 g 1,4-bis-[2-(5-tert.-butyl-7-oct-3-en-2-yl-benzoxazol)-yl]-benzene (see Example 8) and a trace of Pd 5% on carbon catalyst (Fluka) in 20 ml of hexane. The mixture was hydrogenated for 4 hours under hydrogen atmosphere. Then the reaction mixture was filtered and concentrated to yield quantitatively a liquid. UV(EtOH) 350 nm (E=804), 368 nm (E=518).

The product was easily mixable with conventional cosmetic solvents. This product was irradiated in high dilution with a Hg-lamp 150 W (Heraeus) and was shown to be photostable.

EXAMPLE 12

Further Compounds of Formula I that can be Obtained in Accordance with the Preceeding Examples are 1,4-bis-[2-(5-methyl-7-oct-2-yl-benzoxazol)-yl]-benzene;
1,4-bis-[2-(4-tert.-butyl-7-oct-2-yl-benzoxazol)-yl]-benzene;
1,4-bis-[2-(5-tert.-.butyl-7-oct-2-yl)-benzoxazol)-yl]-benzene;
1,4-bis-[2-(4-resp.5-tert.-pentyl-7-oct-2-yl-benzoxazol)-yl]-benzene;
1,4-bis-[2-(5-tert.-butyl-7-hex-2-yl-benzoxazol)-yl]-benzene; and
1,4-bis-[2-(5-tert.-butyl-7-pent-2-yl-benzoxazol)-yl]-benzene.

EXAMPLE 13

Preparation of a O/W Sunscreen Lotion UV-B and UV-A

| | Broad spectrum sunscreen lotion containing 1.5% of a compound of formula I. | |
|---|---|---|
| Recipe [%] | compound | chemical name |
| Part A | | |
| 4 | PARSOL MCX | octyl methoxycinnamate |
| 1.5 | compound of formula I | |

Broad spectrum sunscreen lotion containing 1.5% of a compound of formula I.

| Recipe [%] | compound | chemical name |
|---|---|---|
| 1.5 | PARSOL 1789 | 4-t-butyl-4'-methoxy-dibenzoyl-methane |
| 12 | Cétiol LC | coco-caprylate/caprate |
| 4 | Dermol 185 | Isostearyl neopentanoate |
| 0.25 | diethyleneglycol monostearate | PEG-2-stearate |
| 1 | Cetylalcohol | Cetylalcohol |
| 0.25 | MPOB/PPOB | Methyl-propylparabene |
| 0.1 | EDTA BD | EDTA-sodium salt |
| 1 | Amphisol DEA (Giv.) | Diethanolamine cetylphosphate |
| Part B | | |
| 20 | Permulene TR-1 (+ %) | Acrylate C10–C30 alkylacrylate |
| 48.6 | water deion. | water deion. |
| 5 | Propyleneglycol | 1,2-propanediol |
| 0.8 | KOH (10%) | potassium hydroxyde |

Part A is heated in a reactor to 85° C.
Part B is slowly added within 10 min, followed by addition of KOH, cooling and degassing of the emulsion.

EXAMPLE 14

Preparation of a O/W Anionic Sunscreen Lotion UV-B and UV-A

Broad spectrum sunscreen lotion containing 3% of a compound of formula I.

| Recipe [%] | compound | chemical name |
|---|---|---|
| Part A | | |
| 5 | PARSOL MCX | octyl methoxycinnamate |
| 3 | product of formula I | |
| 4 | PARSOL 500 | 4-methylbenzylidene camphor |
| 2 | PARSOL 1789 | 4-t-butyl-4'-methoxy-dibenzoyl-methane |
| 2 | Glyceryl monostearate | glyceryl stearate |
| 2 | Cetyl alcohol extra | cetyl alcohol |
| 2 | Ganex V-220 | PVP/eicosene copolymer |
| 4 | Ceraphyl 375 | isostearyl neopentanoate |
| 4 | Ceraphyl 847 | octyldodecyl stearoyl stearate |
| 2 | Amphisol K (Giv.) | potassium cetylphosphate |
| 0.1 | Edeta BD | disodium EDTA |
| 0.6 | Phenonip | phenoxyethanol & methyl-, ethyl-, propyl- & butyl-paraben |
| Part B | | |
| 11.15 | water deion. | water deion. |
| 50 | Carbopol 934 1% solution | Carbomer |
| 5 | Propyleneglycol | 1,2-propanediol |
| 0.15 | Nipagin M | methylparaben |
| 3 | KOH (10%) | potassium hydroxyde |
| q.s. | Perfume oil | Fragrance |

Part A is heated in a reactor to 85° C. When homogeneous, add Part B, followed by addition of preheated KOH (75° C.), cooling and degassing of the emulsion.

What is claimed is:

1. A compound of formula III

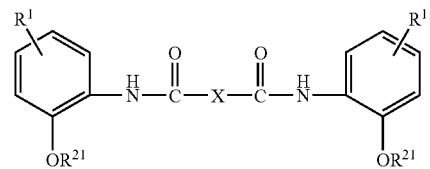

(III)

wherein $R^1$ is hydrogen, $C_{1-20}$alkyl or $C_{2-20}$alkenyl; $R^{21}$ is $-C(R^4,R^5)C(R^6)=C(R^7,R^8)$, wherein $R^4$, $R^5$, $R^6$, $R^7$ and $R^8$ are independently, hydrogen, $C_{1-10}$alkyl or $C_{2-10}$alkenyl, or $C_{2-10}$alkyl or $C_{3-10}$alkenyl containing at least one oxygen atom interrupting the hydrocarbon chain, and X is phenylene or naphthylene, or substituted phenylene or naphthylene.

* * * * *